US010300289B2

(12) United States Patent
Deehr et al.

(10) Patent No.: US 10,300,289 B2
(45) Date of Patent: *May 28, 2019

(54) IN-HEADER PERIMETER RF ANTENNA

(71) Applicant: Cardiac Pacemakers, Inc., St. Paul, MN (US)

(72) Inventors: Mark G. Deehr, Woodinville, WA (US); David A. Chizek, Brooklyn Park, MN (US); Mahesh Maddali, Cape Elizabeth, MA (US); Dennis Eric Larson, White Bear Township, MN (US); Keith Raymond Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/462,548

(22) Filed: Mar. 17, 2017

(65) Prior Publication Data
US 2017/0252569 A1    Sep. 7, 2017

Related U.S. Application Data

(63) Continuation of application No. 12/579,980, filed on Oct. 15, 2009, now Pat. No. 9,616,241.

(Continued)

(51) Int. Cl.
*A61N 1/372* (2006.01)
*A61B 5/00* (2006.01)
(Continued)

(52) U.S. Cl.
CPC ........ *A61N 1/37229* (2013.01); *A61B 5/0031* (2013.01); *A61N 1/3752* (2013.01);
(Continued)

(58) Field of Classification Search
CPC .. A61N 1/37229; A61N 1/3752; A61N 1/375; H01Q 1/40; H01Q 1/273; H01Q 1/2208
(Continued)

(56) References Cited

U.S. PATENT DOCUMENTS 6,809,701 B2    10/2004  Amundson et al.
7,016,733 B2     3/2006  Dublin et al.
(Continued)

FOREIGN PATENT DOCUMENTS

JP    2008537386    9/2008
WO    2010045464    4/2010

OTHER PUBLICATIONS

"Communication Pursuant to Article 94(3) EPC," for European Patent Application No. 09741141.7, dated Aug. 17, 2016 (5 pages).
(Continued)

*Primary Examiner* — Michael W Kahelin
*Assistant Examiner* — Minh Duc G Pham
(74) *Attorney, Agent, or Firm* — Pauly, DeVries Smith & Deffner LLC

(57) ABSTRACT

This document discusses, among other things, an implantable dielectric compartment including a channel in an outer surface of the implantable dielectric compartment, the channel configured to constrain a portion of an implantable antenna in a specific configuration along the length of the portion of the implantable antenna. In certain examples, the implantable antenna can be configured to wirelessly transfer information electromagnetically at a specified operating frequency provided using the specific configuration of the portion of the implantable antenna.

18 Claims, 5 Drawing Sheets

Related U.S. Application Data

(60) Provisional application No. 61/228,109, filed on Jul. 23, 2009, provisional application No. 61/106,068, filed on Oct. 16, 2008.

(51) Int. Cl.
  *A61N 1/375* (2006.01)
  *H01Q 1/22* (2006.01)
  *H01Q 1/27* (2006.01)
  *H01Q 1/40* (2006.01)

(52) U.S. Cl.
  CPC ........... *H01Q 1/2208* (2013.01); *H01Q 1/273* (2013.01); *H01Q 1/40* (2013.01); *A61N 1/375* (2013.01)

(58) Field of Classification Search
  USPC .......................................................... 607/60
  See application file for complete search history.

(56) References Cited

U.S. PATENT DOCUMENTS

| | | | |
|---|---|---|---|
| 7,317,946 | B2 | 1/2008 | Twetan et al. |
| 7,319,901 | B2 | 1/2008 | Dublin et al. |
| 7,467,014 | B2 | 12/2008 | Fuller et al. |
| 7,483,752 | B2 | 1/2009 | Von Arx et al. |
| 8,195,305 | B2 | 6/2012 | Nghiem et al. |
| 9,616,241 | B2 | 4/2017 | Deehr et al. |
| 2004/0233653 | A1 | 11/2004 | Luo et al. |
| 2005/0134520 | A1* | 6/2005 | Rawat ................ A61N 1/37229 343/873 |
| 2005/0203584 | A1* | 9/2005 | Twetan ................ A61B 5/0031 607/36 |
| 2006/0224206 | A1 | 10/2006 | Dublin et al. |
| 2006/0247712 | A1* | 11/2006 | Fuller ................ A61N 1/37229 607/32 |
| 2006/0284770 | A1 | 12/2006 | Jo et al. |
| 2007/0100385 | A1 | 5/2007 | Rawat et al. |
| 2007/0288065 | A1 | 12/2007 | Christman et al. |
| 2007/0288066 | A1 | 12/2007 | Christman et al. |
| 2008/0303728 | A1 | 12/2008 | Lee et al. |
| 2008/0303743 | A1 | 12/2008 | Park et al. |
| 2009/0270948 | A1 | 10/2009 | Nghiem et al. |
| 2010/0099959 | A1 | 4/2010 | Deehr et al. |
| 2010/0100157 | A1 | 4/2010 | Nghiem et al. |
| 2010/0114247 | A1 | 5/2010 | Snitting et al. |
| 2012/0001812 | A1 | 1/2012 | Zhao et al. |
| 2012/0130206 | A1 | 5/2012 | Vajha et al. |

OTHER PUBLICATIONS

File History for U.S. Appl. No. 14/579,980, filed Apr. 3, 2017 (385 pages).

"First Examiner's Report," for Australian Patent Application No. 2009305684 dated Jun. 4, 2012 (2 pages).

"International Preliminary Report on Patentability," for PCT/US2009/60851 dated Apr. 28, 2011 (9 pages).

"International Search Report and Written Opinion," for PCT/US2009/060851 dated Dec. 15, 2009 (15 pages).

"Office Action," for Japanese Patent Application No. 2011-532252 dated Nov. 20, 2012 (6 pages) with English translation.

"Response to Communication Pursuant to Article 94(3) EPC," for European Patent Application No. 09741141.7, filed with the EPO Nov. 7, 2016 (42 pages).

"Response to Communication Pursuant to Rules 161(1) and 162 EPC," for European Patent Application No. 09741141.7 filed with the EPO Jan. 24, 2012 (4 pages).

"Response to Examiner's Report," for Australian Patent Application No. 2009305684 filed Dec. 12, 2012 (31 pages).

* cited by examiner

IN-HEADER PERIMETER RF ANTENNA

CROSS-REFERENCE TO RELATED APPLICATIONS

This application is a continuation of U.S. application Ser. No. 12/579,980, filed on Oct. 15, 2009, which claims the benefit of U.S. Provisional Application No. 61/106,068, filed on Oct. 16, 2008 and U.S. Provisional Application No. 61/228,109, filed on Jul. 23, 2009 under 35 U.S.C. § 119(e), which are hereby incorporated by reference in their entirety.

BACKGROUND

Medical devices can be implanted in a body to perform tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a cardioverter or defibrillator, a neurological stimulator, a neuromuscular stimulator, or a drug delivery system. In certain examples, the implantable medical device can include a telemetry circuit and an antenna, coupled to the telemetry circuit, the combination of which can be configured to provide wireless communication between the implantable medical device and an external device, e.g., to send information (such as physiological or other information) from the implantable medical device to the external device, or to receive information (e.g., such as programming instructions) at the implantable medical device from the external device.

Magnetic coupling can be used to provide short-range (e.g., a few centimeters) communication between an implantable medical device implanted in a body and an external device, or between an implantable medical device outside of the body and an external device. However, magnetic coupling communication largely relies on near-field radiation, where the field distribution is highly dependent upon the distance from, and orientation of, the antenna, which grossly limits the effective range of wireless communication between the implantable medical device and the external device.

As an alternative to magnetic coupling, or in addition to magnetic coupling, low power radio frequency (RF) communication, having an extended range over magnetic coupling, can be used to provide communication between an implantable medical device and an external device.

OVERVIEW

In an example, an implantable dielectric compartment can include a channel in an outer surface of the implantable dielectric compartment, the channel configured to constrain a portion of an implantable antenna in a specific configuration along the length of the portion of the implantable antenna. In certain examples, the implantable antenna can be configured to wirelessly transfer information electromagnetically at a specified operating frequency provided using the specific configuration of the portion of the implantable antenna.

In Example 1, a system includes an implantable dielectric compartment coupled to an implantable device housing, the implantable dielectric compartment including a channel in an outer surface of the implantable dielectric compartment, wherein the channel is configured to constrain a portion of an implantable antenna in a specific configuration along the length of the portion of the implantable antenna, and wherein the implantable antenna is configured to wirelessly transfer information electromagnetically at a specified operating frequency, the specified operating frequency provided using the specific configuration of the portion of the implantable antenna.

In Example 2, the channel of Example 1 optionally includes a narrow portion having a cross section area smaller than a cross section area of the implantable antenna, the narrow portion configured to position the implantable antenna inside the channel.

In Example 3, the implantable antenna of Example 2 optionally includes a polymer covering the portion of the implantable antenna, the polymer providing interference fit in the narrow portion of the channel, the channel sized and shaped to provide a specific configuration for the implantable antenna.

In Example 4, the implantable antenna of any one or more of Examples 1-3 is optionally configured to wirelessly transfer information electromagnetically from within a biological medium using a specified operating frequency, the specified operating frequency provided using the specific configuration of the implantable antenna in the biological medium.

In Example 5, the implantable dielectric compartment of any one or more of Examples 1-4 optionally includes a cap coupled to the channel, the cap configured to cover the portion of the implantable antenna along the channel, and the implantable dielectric compartment of any one or more of Examples 1-4 optionally includes a first interlocking feature and the cap includes a second interlocking feature, the first and second interlocking features configured to couple the cap to the channel In Example 6, the channel and the cap of Example 5 are optionally configured to establish a specified distance between the portion of the implantable antenna and the biological medium, the specified distance configured to control an impedance of the implantable antenna.

In Example 7, the channel of any one or more of Examples 5-6 optionally includes a tapered channel, and wherein the cap is configured to position the portion of the implantable antenna in a specific configuration inside the tapered channel.

In Example 8, the implantable antenna of any one or more of Examples 5-7 optionally includes a wire antenna configured to be positioned in the channel, the implantable dielectric compartment of any one or more of Examples 5-7 optionally includes a third interlocking feature and the cap includes a fourth interlocking feature, the third and fourth interlocking features separate from the first and second interlocking features, and the first and second interlocking features of any one or more of Examples 5-7 are optionally configured to couple the cap to the channel at a first point over the implantable antenna, and wherein the second and third interlocking features are configured to couple the cap to the channel at a second point, wherein the distal end of the implantable antenna is configured to be located substantially between the first and second points, such that the first, second, third, and fourth interlocking features are configured to secure the distal end of the implantable antenna in the channel.

In Example 9, the implantable dielectric compartment of Example 8 optionally includes a fifth interlocking feature and the cap of Example 8 optionally includes a sixth interlocking feature, the fifth and sixth interlocking features separate from the first, second, third, and fourth interlocking features, wherein the fifth and sixth interlocking features are configured to couple the cap to the channel at a third point, wherein the first and second points are located on a first side of the implantable dielectric compartment and the third point is located on a second side of the implantable dielectric compartment, the second side different from the first side.

In Example 10, the first, third, and fifth interlocking features of Example 9 optionally include female connectors and the second, fourth, and sixth interlocking features of Example 9 optionally include male connectors.

In Example 11, the implantable dielectric compartment of any one or more of Examples 1-10 optionally includes a first receptacle and a second receptacle, the first receptacle configured to receive a first lead and the second receptacle configured to receive a second lead, the first receptacle closer to the implantable medical device housing than the second receptacle, and the channel of any one or more of Examples 1-10 is optionally located in the outer surface of the implantable dielectric compartment substantially between first and second receptacles.

In Example 12, the implantable dielectric compartment of Example 11 optionally includes a third receptacle, the third receptacle configured to receive a third lead, the second receptacle closer to the implantable medical device housing than the third receptacle.

In Example 13, a system includes an implantable dielectric compartment coupled to an implantable device housing, the implantable dielectric compartment including a tapered channel in an outer surface of the implantable dielectric compartment, the tapered channel configured to constrain a portion of an implantable antenna in a specific configuration along the length of the portion of the implantable antenna, a cap coupled to the tapered channel, the cap configured to cover the portion of the implantable antenna along the tapered channel and to contain the portion of the implantable antenna in the specific configuration along the inside of the tapered channel, wherein the implantable antenna includes a wire antenna having a polymer covering the portion of the implantable antenna, and wherein the tapered channel includes a narrow portion having a cross section area smaller than a cross sectional area of the polymer covering the implantable antenna, the narrow portion providing an interference fit with the polymer, the narrow portion configured to position the implantable antenna within the tapered channel, wherein the implantable antenna is configured to wirelessly transfer information electromagnetically using a specified operating frequency provided using the specific configuration of the implantable antenna, wherein the implantable dielectric compartment includes a first interlocking feature and the cap includes a second interlocking feature, the first and second interlocking features configured to couple the cap to the tapered channel at a first point over the implantable antenna, wherein the implantable dielectric compartment includes a third interlocking feature and the cap includes a fourth interlocking feature, the third and fourth interlocking features configured to couple the cap to the tapered channel at a second point, the third and fourth interlocking features separate from the first and second interlocking features, and wherein the distal end of the implantable antenna is configured to be located substantially between the first and second points, such that the first, second, third, and fourth interlocking features are configured to secure the distal end of the implantable antenna in the tapered channel.

In Example 14, the implantable dielectric compartment of Example 13 optionally includes a fifth interlocking feature and the cap of Example 13 optionally includes a sixth interlocking feature, the fifth and sixth interlocking features separate from the first, second, third, and fourth interlocking features, wherein the fifth and sixth interlocking features are configured to couple the cap to the tapered channel at a third point, wherein the first and second points are located on a first side of the implantable dielectric compartment and the third point is located on a second side of the implantable dielectric compartment, the second side different from the first side.

In Example 15, a method includes providing a tapered channel in an outer surface of an implantable dielectric compartment, the tapered channel configured to constrain a portion of an implantable antenna in a specific configuration along the length of the portion of the implantable antenna, wirelessly transferring information electromagnetically at a specified operating frequency using the implantable antenna, the specified operating frequency provided using the specific configuration of the portion of the implantable antenna.

In Example 16, the wirelessly transferring information electromagnetically of Example 15 optionally includes wirelessly transferring information electromagnetically at a specified operating frequency from within a biological medium using the implantable antenna, the specified operating frequency provided using the specific configuration of the portion of the implantable antenna in the biological medium.

In Example 17, the method of any one or more of Examples 15-16 optionally includes providing a narrow portion in the tapered channel having a cross section area smaller than a cross section area of the implantable antenna, the narrow portion configured to position the implantable antenna inside the tapered channel.

In Example 18, the method of any one or more of Examples 15-17 optionally includes providing an interference fit between a polymer covering the portion of the implantable antenna and the narrow portion of the tapered channel, wherein the tapered channel is sized and shaped to provide the specific configuration for the implantable antenna.

In Example 19, the method of any one or more of Examples 15-18 optionally includes providing a cap configured to cover the portion of the implantable antenna in the tapered channel and to position the implantable antenna in the specific configuration inside the tapered channel, the cap coupled to the tapered channel using a first interlocking feature of the implantable dielectric compartment and a second interlocking feature of the cap.

In Example 20, the cap of Example 19 is optionally coupled to the tapered channel at a first point over the implantable antenna using the first and second interlocking features and at a second point using the third and fourth interlocking features, the implantable antenna of Example 19 optionally includes a wire antenna, the distal end of the wire antenna configured to be located substantially between the first and second points.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
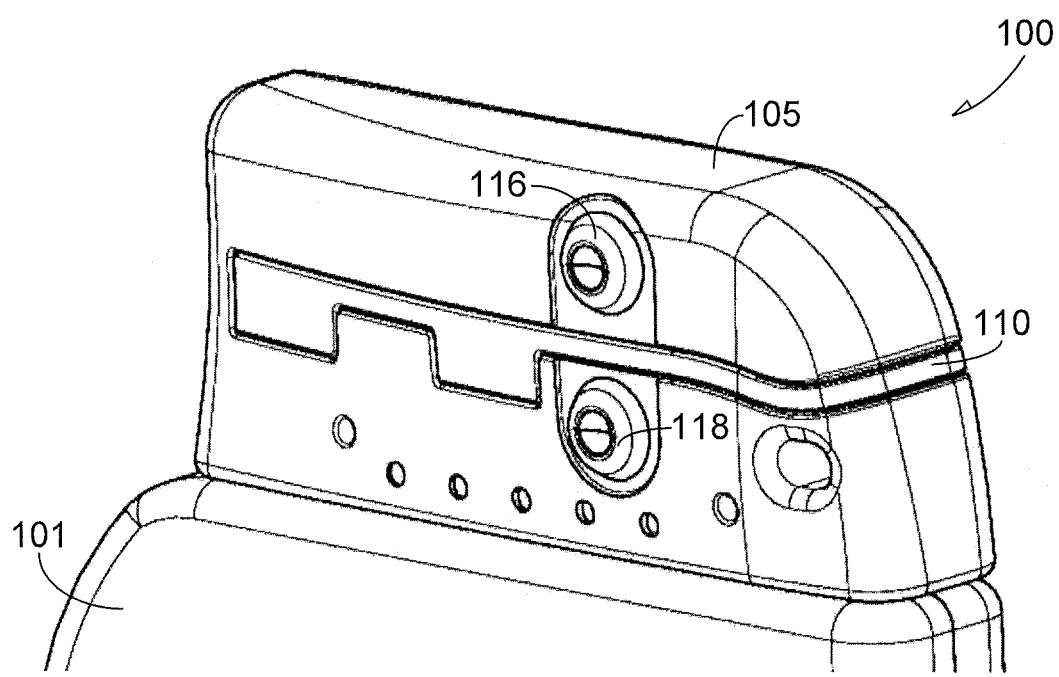
FIG. 1 illustrates generally an example of a system including an implantable antenna coupled to an implantable telemetry circuit.

In an example, an implantable antenna (e.g., a wire antenna covered in a polyurethane tube or one or more other dielectrics) can be located in a channel in an outer surface of an implantable dielectric compartment (e.g., header) of an implantable medical device (e.g., pacemaker, defibrillator, etc.). The implantable antenna can be configured to wirelessly transfer information electromagnetically at a specified operating frequency. In an example, the specified operating frequency can be provided using one or more characteristics of the implantable antenna (e.g., the length of the implantable antenna, the shape of the implantable antenna, the proximity of the implantable antenna to one or more other conductors in the implantable medical device, etc.).

In certain examples, positioning the implantable antenna about the perimeter or outer surface of the implantable dielectric compartment can increase the radio frequency efficiency of the implantable antenna or decrease losses due to metallic objects within the implantable dielectric compartment (e.g., one or more receptacles, leads, connector blocks, x-ray identification tags, anchor posts, etc.). In certain examples, the channel can be configured to constrain a portion of the implantable antenna in a specific configuration. In an example, at least one of a length of the implantable antenna, the specific configuration (e.g., shape, path, etc.) of the implantable antenna, or a distance between the implantable antenna and one or more other conductive components in the implantable dielectric compartment can be controlled to provide wireless communication at a specified operating frequency, or to increase the effectiveness of the implantable antenna at the specified operating frequency.

In an example, if the implantable antenna is only covered in the channel with a medical adhesive or other fill material, the reliability or repeatability of radiofrequency communication (e.g., range, efficiency, etc.) across multiple devices can diminish due to varying medical adhesive or other fill material thickness (medical adhesive thickness can vary between different operators, machines, processes, etc.). In an example, for a desired material thickness of 30 thousandths of an inch over the implantable antenna, medical adhesive applied by hand can vary by +30 to −10 thousandths of an inch or more. In other examples, a machine or process (e.g., robotics) can reduce the variance to %10 of that applied by hand (e.g., ±3 thousandths of an inch). In certain examples, a cap (e.g., an injection molded thermoplastic or other dielectric material cap) can further alleviate the variance of the medical adhesive or other fill material (e.g., to ±2 thousandths of an inch or less), establishing a more precise distance between the implantable antenna and the body. Further, in certain examples, the cap can be used to establish a repeatable specific configuration for the implantable antenna (e.g., using one or more features of the implantable dielectric compartment, the channel, or the cap).

In other examples, the reliability or repeatability of radiofrequency communication across multiple devices can diminish due to varying implantable antenna placement or configuration. In an example, the channel can be sized and shaped to constrain the implantable antenna in a specific configuration. In certain examples, the specific configuration can affect the resonant frequency or the efficient operating point of the implantable antenna. In an example, by providing the specific configuration, the implantable antenna can maintain a specified distance from one or more other conductors in the implantable dielectric compartment.

In an example, the implantable antenna to body (e.g., fluid, tissue, or one or more other biological medium) interaction can be maintained using a specified depth of the channel and the specified thickness of the cap. In an example, the spacing between the implantable antenna and a biological medium can affect the impedance of the implantable antenna. By improving the control of the impedance, the implantable antenna range or efficiency can be improved or can become more repeatable across multiple devices.

In other examples, the channel can include a tapered channel configured to constrain the implantable antenna in a specific configuration at the bottom or center of the tapered channel. In certain examples, by providing a specific configuration of the implantable antenna, one or more fundamental or resonant operating frequencies can be more easily repeated or attained (e.g., across multiple devices, etc.).

In certain examples, the implantable antenna can be covered by a polymer or other dielectric material (e.g., inserted into a polyurethane tube to isolate the implantable antenna from external shocks, etc.) and then inserted into the channel in the implantable dielectric compartment. In an example, medical adhesive can be applied to the channel before or after inserting the implantable antenna into the channel. In an example, the cap can be coupled to the channel using the medical adhesive or one or more interlocking features.

In certain examples, an identical or substantially identical channel, cap, or implantable antenna can be used among different implantable medical devices (e.g., a family of devices having a different number or receptacles, etc.) communicating at the same specified operating frequency.

In an example, a first implantable medical device can include a single set of receptacles, the single set of receptacles for the first implantable medical device consisting of a first number of receptacles (e.g., a first receptacle and a second receptacle), and a second implantable medical device can include a single set of receptacles, the single set of receptacles for the second implantable medical device consisting of a second number of receptacles (e.g., a first receptacle, a second receptacle, and a third receptacle). In this example, an identical or substantially identical channel, cap, or implantable antenna can be used for each of the first and second implantable medical devices.

In an example, in a two-receptacle implantable medical device, the channel can be located on an outer surface of the implantable dielectric compartment substantially between the first and second receptacles. In certain examples, a three-receptacle implantable medical device can include a third receptacle (or one or more other receptacles) added, for example, above the first and second receptacles of the two-receptacle implantable medical device, without changing the width of the implantable dielectric compartment, or without changing the orientation of the first and second receptacles with respect to the first implantable medical device. In these examples, an identical or substantially identical channel, cap, or implantable antenna can be used to wirelessly transfer information electromagnetically at a specified operating frequency among different devices, saving manufacturing and design costs, and adding reliability in communication among the different devices.

FIG. 1 illustrates generally an example of a system 100 including an implantable dielectric compartment 105 coupled to an implantable medical device housing 101 and a cap 110 coupled to a channel in an outer surface of the implantable dielectric compartment 105.

In the example of FIG. 1, the implantable dielectric compartment 105 includes first and second receptacles configured to receive respective first and second leads. The implantable dielectric compartment 105 includes a first fastener 118 (e.g., set screw, etc.) configured to secure the first lead in the first receptacle and second fastener 116 configured to secure the second lead in the second receptacle. In an example, the first receptacle, the second receptacle, or one or more other receptacles can include one or more connector blocks configured to provide an electrical contact between electronics in the implantable medical device housing 101 and an electrical contact on one or more leads. In other examples, the implantable dielectric compartment 105 can include a different number of receptacles (e.g., a single receptacle, three-receptacles, etc.).

In the example of FIG. 1, the first receptacle is located closer to the implantable medical device housing 101 than the second receptacle. In an example, the channel and the cap 110 can be located substantially between the first receptacle and the second receptacle, such that an implantable antenna in the channel can be configured to be located a certain distance (e.g., 50 thousandths of an inch, etc.) from one or more other conductive structures of the system 100 (e.g., implantable medical device housing 101, the first fastener 118, the second fastener 116, one or more connector blocks, one or more leads, leads, etc.), such as to reduce interference by the one or more other conductive structures.

In other examples, the implantable dielectric compartment 105 can include one or more other receptacles configured to receive one or more other leads. For example, the implantable dielectric compartment 105 can include a third receptacle configured to receive a third lead, and a third fastener configured to secure the third lead in the third receptacle. In an example, the second receptacle can be located closer to the implantable medical device housing 101 than the third receptacle. In these examples, the cap 110 can be located in an identical or substantially identical position as the cap illustrated in the example of FIG. 1. Further, in these examples, the cap 110, the channel, or the implantable antenna can be identical or substantially identical (e.g., in shape, position, configuration, etc.) as illustrated in the example of FIG. 1.

Figure 2A:
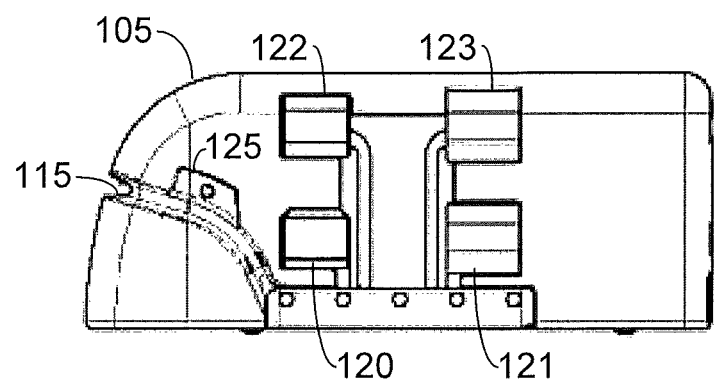
FIGS. 2A and 2B illustrate generally different views of an example of an implantable dielectric compartment including a channel in an outer surface of the implantable dielectric compartment.
Figure 2B:
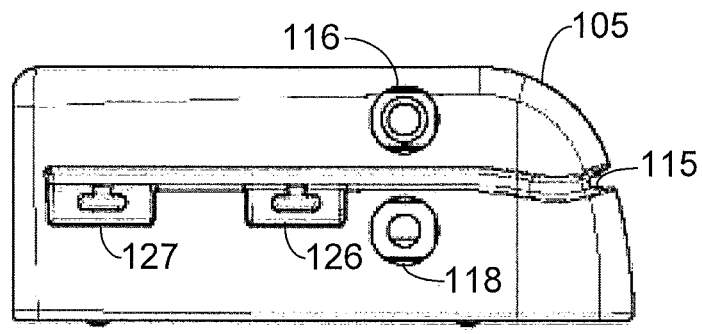
Figure 3A:
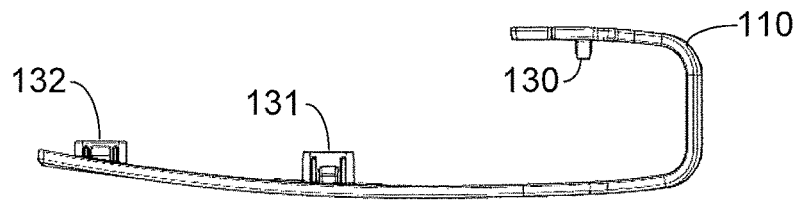
FIGS. 3A-3F illustrate generally different views of an example of a cap configured to be coupled to a channel of an implantable dielectric compartment.
Figure 3B:
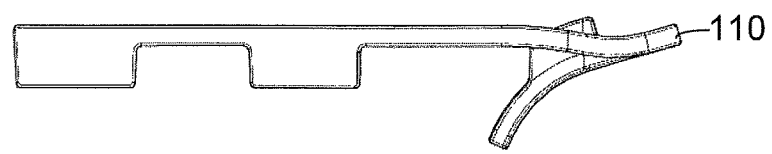
Figure 3C:
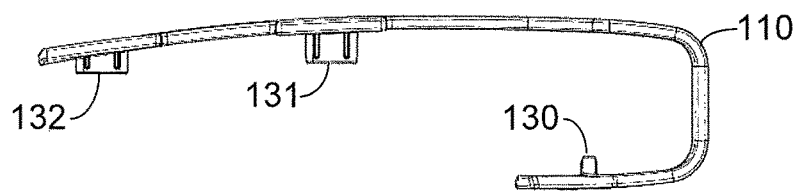
Figure 3D:
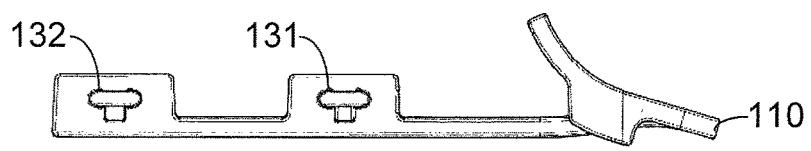
Figure 3E:
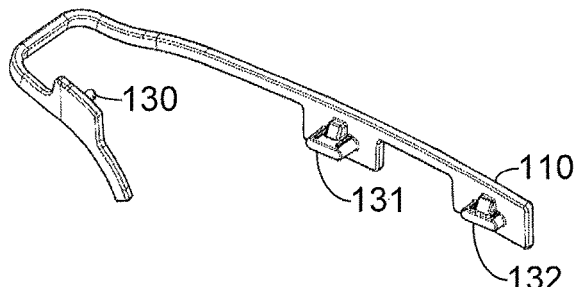
Figure 3F:
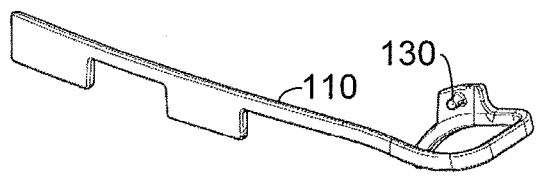

FIGS. 2A and 2B illustrate generally different views of an example of an implantable dielectric compartment 105 including a channel 110 in an outer surface of the implantable dielectric compartment 105. FIG. 2A illustrates generally a first side, and FIG. 2B illustrates generally a second side, of the implantable dielectric compartment 105. In an example, the proximate end of the channel 115 can be located (as illustrated in FIG. 2A) at or near a feed-through configured to provide access from the implantable dielectric compartment 105 to electronic circuitry (e.g., a telemetry circuit, a processor, etc.) in the implantable medical device housing. The channel 115 can progress away from the implantable medical device housing and around the perimeter of the implantable dielectric compartment 105 to the second side of the implantable dielectric compartment 105 (as illustrated in FIG. 2B). In certain examples, the channel 115 can be formed during the manufacturing process of the implantable dielectric compartment 105 (e.g., during injection molding of the implantable dielectric compartment 105).

In the example of FIG. 2B, the channel 115 is located substantially between the first fastener 118 and the second fastener 116. In an example, the path of the channel 115 can be configured to maximize a distance or provide a minimum spacing between an implantable antenna configured to be positioned or located in the channel and one or more other conductors (e.g., fasteners, connector blocks, the implantable medical device housing, etc.).

In an example, the implantable dielectric compartment 105 can include a first connector block 120 and a second connector block 121 configured to provide an electrical contact between electronic circuitry in the implantable medical device housing and an electrical contact on a first lead. Further, the implantable dielectric compartment 105 can include a third connector block 122 and a fourth connector block 123 configured to provide an electrical contact between electronic circuitry in the implantable medical device housing and an electrical contact on a second lead. In an example, the first connector block 120 and the second connector block 121 can be coupled to a first lead located in a first receptacle of the implantable dielectric compartment 105, and the third connector block 122 and the fourth connector block 123 can be coupled to a second lead located in a second receptacle of the implantable dielectric compartment 105. In other examples, the implantable dielectric compartment 105 can include one or more other connector blocks, or a different number of connector blocks.

In certain examples, the implantable dielectric compartment 105 can include one or more interlocking features configured to interact with one or more features of a cap to couple the cap to the channel 115. In an example, the one or more interlocking features of the implantable dielectric compartment 105 can be located on or proximate to the channel 115. In the examples of FIGS. 2A and 2B, the one or more interlocking features include a first interlocking feature 125 on the first side of the implantable dielectric compartment 105, and a second interlocking feature 126 and a third interlocking feature 127 on the second side of the implantable dielectric compartment 105. In other examples, one or more other interlocking features or a different number of interlocking features can be used.

FIGS. 3A-3F illustrate generally different views of an example of a cap 110 configured to be coupled to a channel of an implantable dielectric compartment. In certain examples, the cap 110 can include an injection molded cap. In an example, the cap 110 can be configured to cover a portion of an implantable antenna along the channel. In an example, the cap 110 can include one or more interlocking features configured to interact with one or more features of the channel to couple the cap 110 to the channel. In the examples of FIGS. 3A-3F, the one or more interlocking features include a first interlocking feature 130 on a first side of the cap 110, and a second interlocking feature 131 and a third interlocking feature 132 on a second side of the channel 110. In an example, the first interlocking feature 130 of the cap 110 can be configured to interlock with a first interlocking feature of the implantable dielectric compartment (e.g., the first interlocking feature 125 of the implantable dielectric compartment of FIG. 2A).

In an example, the first interlocking feature 130 of the cap 110 can include a male connector configured to interact with a female connector on the implantable dielectric compartment. In other examples, the first interlocking feature 130 of the cap 110 can include a female connector or one or more other connectors configured to interact with a corresponding connector on the implantable dielectric compartment or the channel (e.g., a screw and a threaded portion, etc.).

Figure 4A:
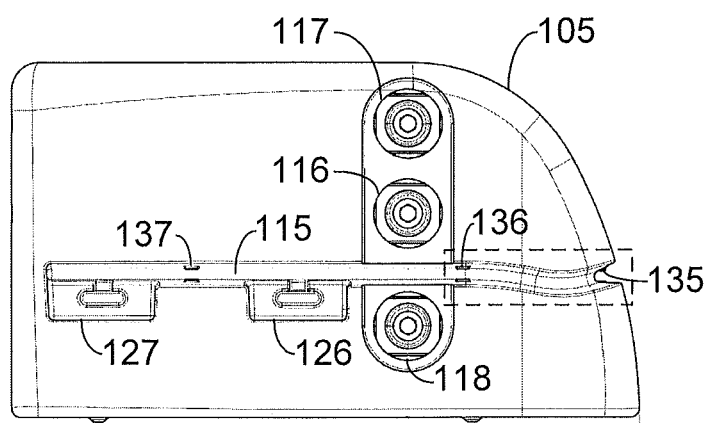
FIGS. 4A and 4B illustrate generally an example of an implantable dielectric compartment including a channel in an outer surface of the implantable dielectric compartment.
Figure 4B:
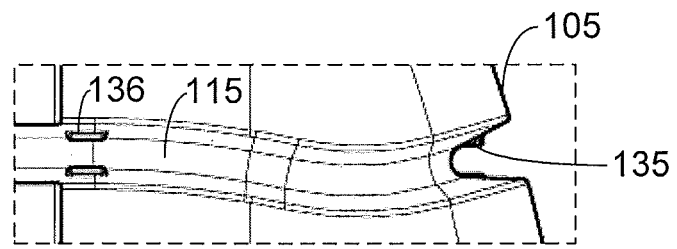

FIGS. 4A and 4B illustrate generally an example of an implantable dielectric compartment 105 including a channel 115 in an outer surface of the implantable dielectric compartment 105. In the example of FIG. 4A, the implantable dielectric compartment 105 includes first, second, and third receptacles configured to receive respective first, second, and third leads. In an example, the implantable dielectric compartment 105 can include a first fastener 118 configured to secure the first lead in the first receptacle, a second fastener 116 configured to secure the second lead in the second receptacle, and a third fastener 117 configured to secure the third lead in the third receptacle. In certain examples, the implantable dielectric compartment 105 can include one or more interlocking features (e.g., a second interlocking feature 126 and a third interlocking feature 127) configured to interface with one or more features of a cap to couple the cap to the channel 115, and to contain the implantable antenna in a specific configuration in the channel 115.

In an example, the channel 115 can be configured to constrain a wire antenna placed in the channel 115. In certain examples, the distal end of the wire antenna can tend to protrude from the channel 115 during placement of the wire antenna. In certain examples, the second interlocking feature 126 and the third interlocking feature 127 can be located on either side of the distal end of the wire antenna, and can be configured to secure the distal end of the wire antenna in place in the channel 115.

In an example, the channel 115 can include one or more narrow portions (e.g., pinch points, etc.) configured to position the implantable antenna inside the channel 115. In the example of FIG. 4A, the channel 115 includes a first narrow portion 135, a second narrow portion 136, and a third narrow portion 137. In an example, the one or more narrow portions can have a cross section area smaller than a cross section area of the implantable antenna. In certain examples, using a wire antenna, the third narrow portion 137 can be configured to secure the distal end of the wire antenna in the channel 115.

FIG. 4B illustrates generally an example of a side view of the first narrow portion 135 in the channel 115, and the second narrow portion 136 in the channel 115. In an example, the one or more narrow portions can be configured to provide an interference fit with the implantable antenna.

In an example, the implantable antenna can include a polymer or other dielectric material covering a portion of the implantable antenna configured to be located in the channel 115. In certain examples, the polymer can include a polyurethane tube or one or more other polymers or dielectrics. In an example, the narrow portion can be configured to provide the interference fit with the polymer covering the implantable antenna instead of or in conjunction with providing the interference fit with the implantable antenna (e.g., a wire antenna).

In certain examples, the channel 115 can be sized and shaped to provide a specific configuration for the implantable antenna. In an example, one or more narrow portions can be configured to maintain the specific configuration of the implantable antenna in the channel 115.

Figure 5:
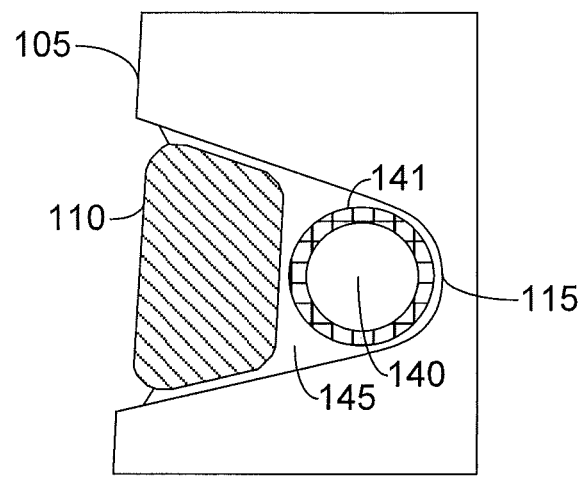
FIG. 5 illustrates generally an example of an implantable dielectric compartment having a channel in an outer surface of the implantable dielectric compartment, the channel configured to constrain a portion of an implantable antenna, the implantable antenna including a polymer covering the portion of the implantable antenna.

FIG. 5 illustrates generally an example of an implantable dielectric compartment 105 having a channel 115 in an outer surface of the implantable dielectric compartment 105, the channel 115 configured to constrain a portion of an implantable antenna 140 in a specific configuration along the length of the portion of the implantable antenna. The implantable antenna 140 can include a polymer 141 covering the portion of the implantable antenna 140, and a cap 110 can be configured to contain the implantable antenna 140 in the channel 115. In an example, the channel 115 can include a tapered channel, sized and shaped to provide a specific configuration (e.g., antenna shape and route) for the implantable antenna 140. In certain examples, the sides of the tapered channel can be configured to constrain the length of the portion of the implantable antenna (e.g., the entire length of the portion of the implantable antenna 140 in the channel 115), such as illustrated by the cross-section view in the example of FIG. 5. In an example, the shape or diameter of the base of the channel 115 can be the same as or approximately equal to (e.g., in certain examples, slightly larger or smaller) one of the shape or diameter of the implantable antenna 140 or the polymer 141 covering the portion of the implantable antenna 140. In an example, the shape or diameter of the base of the channel 115 can be configured to constrain or provide the specific configuration for the portion of the implantable antenna 140.

In certain examples, a medical adhesive 145 or one or more other fill materials can be placed in the channel 115 before, during, or after the implantable antenna 140 (including the polymer 141 covering the implantable antenna 140) is placed in the channel 115. In the example of FIG. 5, the cap 110 can be placed in the channel 115, the cap 110 configured to cover the portion of the implantable antenna 140 along the channel 115 and to position the portion of the implantable antenna 140 in a specific configuration in the channel (e.g., along the inside of the tapered channel). In an example, the medical adhesive 145 can be configured to hold the implantable antenna 140 in place within the channel 115, to seal the channel 115 from one or more biological medium (e.g., tissue, blood, etc.), or to hold the cap 110 in place over the implantable antenna 140. In an example, the one or more interlocking features of the implantable dielectric compartment 105 and the cap 110 can be configured to hold the cap 110 in place within the channel 115.

In an example, the implantable antenna 140 can be configured to be constrained to an inside edge of the channel 115. In an example, the implantable antenna 140 can include a wire antenna having a circular cross section (e.g., 15 thousandths of an inch), and can be contained in a polyurethane tube (e.g., 20 thousandths of an inch). The implantable antenna 140 and the polyurethane tube can be configured to fit securely inside edge the channel 115 (e.g., a tapered channel).

In an example, the medical adhesive 145 and the cap 110 can be configured to secure the implantable antenna 140 in a specific configuration inside the channel 115. In certain examples, the medical adhesive 145 can be configured to only seal the connection between the cap 110 and the channel 115, and the shape of the channel 115 and the one or more features of the channel 115 (e.g., the one or more narrow portions) can be configured to provide the specific configuration of the implantable antenna 115. In certain examples, the outside surface of the cap 110 can be configured to reside below the outside surface of the implantable dielectric compartment 105 (e.g., 5 thousandths of an inch). In an example, the cap 110 can be configured to fit within the channel 115 having a space between the surfaces of the cap 110 proximate the channel 115 (e.g., 2 thousandths of an inch), the space configured to be filled with medical adhesive 145 to seal the implantable antenna 140 in the channel 115.

In certain examples, the cap 110 can increase the cost of the implantable dielectric compartment 105 (e.g., in contrast to providing medical adhesive or one or more other fill material to the channel 115 instead of the cap 110). Accordingly, in an example, the implantable antenna 140 can be constrained in the channel 115 without using the cap 110. Instead, a machine or process (e.g., robotics) can be configured to provide a uniform or substantially uniform layer of medical adhesive 145 or other fill material to the channel 115 over the implantable antenna 140. In these examples, the one or more interlocking features of the implantable dielectric compartment 105 can be excluded. Instead, one or more narrow portions (e.g., pinch points, etc.) in the channel 115 can be configured to position or retain the implantable antenna 140 in the channel 115.

Further, in other examples, the implantable dielectric compartment 105, the implantable antenna 140, the channel 115, the cap 110, or one or more other component disclosed herein can include one or more other features, functions, or configurations, such as those disclosed in the commonly assigned Nghiem et al. U.S. Patent Application Ser. No. 61/106,068 entitled "IMPEDANCE-CONTROLLED IMPLANTABLE TELEMETRY ANTENNA," which is hereby incorporated by reference in its entirety, including its disclosure of an implantable antenna having a controllable input impedance, or of a cover coupled to an implantable assembly housing.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventor also contemplates examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
an implantable antenna configured to wirelessly transfer information electromagnetically at a specified operating frequency, a specific configuration of the implantable antenna configured to operate at the specified operating frequency; and
an implantable dielectric compartment coupled to a single side of an implantable device housing and the implantable dielectric compartment having an outer surface, the outer surface comprising a first side, a second side opposite the first side, and a third side connecting the first and second sides, the implantable dielectric compartment including:
a channel extending along at least a length of the first side, a length of the second side, and a length of the third side of the outer surface of the implantable dielectric compartment, the length of the channel in the third side less than the length of the channel in at least one of the first and second sides;
wherein the channel is configured to provide the specific configuration to an implantable antenna along the length of the implantable antenna.

2. The system of claim 1, wherein the channel includes a narrow portion having a cross section area smaller than a cross section area of the implantable antenna, the narrow portion configured to position the implantable antenna inside the channel.

3. The system of claim 2, wherein the implantable antenna includes a polymer covering the implantable antenna, the polymer providing an interference fit in the narrow portion of the channel, the channel sized and shaped to provide the specific configuration for the implantable antenna.

4. The system of claim 1, wherein the implantable antenna is configured to wirelessly transfer information electromagnetically from within a biological medium using a specified operating frequency, the specified operating frequency provided using the specific configuration of the implantable antenna in the biological medium.

5. The system of claim 1, wherein the channel is configured to establish a specified distance between the implantable antenna and a biological medium, the specified distance configured to control an impedance of the implantable antenna.

6. The system of claim 1, wherein the channel includes a tapered cross section, and wherein the implantable antenna is positioned in the specific configuration inside the tapered cross section of the channel.

7. The system of claim 1, wherein the implantable dielectric compartment includes a first receptacle and a second receptacle, the first receptacle configured to receive a first lead and the second receptacle configured to receive a second lead, the first receptacle closer to the implantable device housing than the second receptacle; and
wherein the channel is located in the outer surface of the implantable dielectric compartment substantially between first and second receptacles.

8. The system of claim 7, wherein the implantable dielectric compartment includes a third receptacle, the third receptacle configured to receive a third lead, the second receptacle closer to the implantable device housing than the third receptacle.

9. The system of claim 1, wherein the system comprises an adhesive seal configured to seal the implantable antenna in the channel.

10. The system of claim 1, wherein the antenna and the channel are located approximately equidistant from two conductive structures of the implantable dielectric compartment.

11. A system comprising:
an implantable dielectric compartment coupled to an implantable device housing, the implantable dielectric compartment including:
a channel extending along an outer surface of the implantable dielectric compartment including along at least a length of a first side, a length of a second side opposite the first side, and a length of a third side connecting the first and second sides of the outer surface of the implantable dielectric compartment, the length of the channel in the third side less than the length of the channel in at least one of the first and second sides, the channel including a tapered cross section configured to provide a specific configuration to an implantable antenna along the length of the implantable antenna;
a receptacle operable to connect to a lead coupling the dielectric compartment to body tissue;
wherein the implantable antenna includes a wire antenna having a polymer covering the implantable antenna, and wherein the tapered cross section of the channel includes a narrow portion having a cross section area smaller than a cross sectional area of the polymer covering the implantable antenna, the narrow portion providing an interference fit with the polymer, the narrow portion configured to position the implantable antenna within the channel;
wherein the implantable antenna is configured to wirelessly transfer information electromagnetically using a specified operating frequency configured to work with the specific configuration of the implantable antenna.

12. The system of claim 11, wherein the antenna and the channel are located approximately equidistant from two conductive structures of the implantable dielectric compartment.

13. A method comprising:
providing an implantable antenna;
providing a channel extending along an outer surface of an implantable dielectric compartment along at least a length of a first side, a length of a second side opposite the first side, and a length of a third side connecting the first and second sides of the outer surface of the implantable dielectric compartment, the length of the channel in the third side less than the length of the channel in at least one of the first and second sides, the channel including a tapered cross section configured to provide a specific configuration to the implantable antenna along the length of the implantable antenna;
positioning the implantable antenna in the specific configuration inside the channel;
coupling the implantable dielectric compartment to a single side of an implantable medical device; and
wirelessly transferring information electromagnetically at a specified operating frequency using the implantable antenna, the specified operating frequency configured to work with the specific configuration of the implantable antenna.

14. The method of claim 13, wherein the wirelessly transferring information electromagnetically includes wirelessly transferring information electromagnetically at a specified operating frequency from within a biological medium using the implantable antenna, the specified operating frequency provided using the specific configuration of the implantable antenna in the biological medium.

15. The method of claim 13, including providing a narrow portion in the tapered cross section of the channel having a cross sectional area smaller than a cross sectional area of the implantable antenna, the narrow portion configured to position the implantable antenna inside the tapered cross section of the channel.

16. The method of claim 15, including providing an interference fit between a polymer covering the implantable antenna and the narrow portion of the tapered cross section of the channel, wherein the tapered cross section of the channel is sized and shaped to provide the specific configuration for the implantable antenna.

17. The method of claim 13, further comprising providing an adhesive seal configured to seal the implantable antenna in the channel.

18. The method of claim 13, wherein the antenna and the channel are located approximately equidistant from two conductive structures of the implantable dielectric compartment.

* * * * *